United States Patent [19]

Martin

[11] Patent Number: 5,674,829
[45] Date of Patent: Oct. 7, 1997

[54] STABLE AQUEOUS GLUTARALDEHYDE SOLUTIONS CONTAINING SODIUM ACETATE AND A NONIONIC DETERGENT

[75] Inventor: Antoinetta Pamela Martin, Johannesburg, South Africa

[73] Assignee: Antoinetta P. Martin, South Africa

[21] Appl. No.: 590,576

[22] Filed: Jan. 24, 1996

Related U.S. Application Data

[63] Continuation of Ser. No. 187,169, Jan. 27, 1994, abandoned.

[30] Foreign Application Priority Data

Jan. 29, 1993 [ZA] South Africa ............... 93/0662

[51] Int. Cl.$^6$ ............... C11D 1/70; C11D 3/075; C11D 3/22
[52] U.S. Cl. ............... 510/383; 510/382; 510/199; 510/161; 510/131; 422/38
[58] Field of Search ............... 252/106, 174.21, 252/173, DIG. 1, DIG. 5, 91; 422/38; 510/131, 161, 199, 382, 383

[56] References Cited

U.S. PATENT DOCUMENTS

| | | | |
|---|---|---|---|
| 3,016,328 | 1/1962 | Pepper | 167/22 |
| 3,282,775 | 11/1966 | Stonehill | 167/22 |
| 3,912,450 | 10/1975 | Boucher | 21/54 A |
| 3,968,248 | 7/1976 | Boucher | 424/333 |
| 3,968,250 | 7/1976 | Boucher | 424/333 |
| 3,983,252 | 9/1976 | Buchalter | 424/333 |
| 4,048,336 | 9/1977 | Winicov et al. | 424/334 |
| 4,093,744 | 6/1978 | Winicov et al. | 424/333 |
| 4,208,404 | 6/1980 | Cowan | 424/153 |
| 4,436,754 | 3/1984 | Jacobs | 424/333 |
| 4,690,772 | 9/1987 | Tell et al. | 252/106 |
| 4,804,685 | 2/1989 | Jacobs | 514/698 |
| 4,896,768 | 1/1990 | Anderson | 206/210 |
| 4,923,899 | 5/1990 | Wachman et al. | 514/642 |
| 5,004,757 | 4/1991 | Boucher | 514/694 |
| 5,130,135 | 7/1992 | Van Tonder | 424/405 |
| 5,158,778 | 10/1992 | Donovan et al. | 424/488 |
| 5,447,684 | 9/1995 | Williams | 422/20 |
| 5,498,858 | 3/1996 | Eggensperger | 514/693 |

FOREIGN PATENT DOCUMENTS

| | | |
|---|---|---|
| 888.601 | 8/1981 | Belgium . |
| 0 066 759 A1 | 5/1982 | European Pat. Off. . |
| 0 207 633 A2 | 6/1986 | European Pat. Off. . |
| 2 622 397 | 11/1987 | France . |
| 2 138 798 | 11/1983 | United Kingdom . |
| WO87/06099 | 4/1987 | WIPO . |
| WO91/00689 | 11/1989 | WIPO . |

*Primary Examiner*—Paul Lieberman
*Assistant Examiner*—Kery A. Fries
*Attorney, Agent, or Firm*—Nath & Associates; Gary M. Nath; Suet M. Chong

[57] ABSTRACT

A stable, aqueous, glutaraldehyde solution comprising:
   an aqueous solution of glutaraldehyde;
   a non-ionic detergent;
   sodium acetate; and
   sufficient of a pH modifier to bring the pH of the solution to 6 to 8.5 is provided.

The solution does not require an activator prior to use and is not a skin irritant. It is also stable for a period of up to 6 months at temperatures of 25° C. when undiluted. When diluted further with water to differing concentrations, it is suitable for use as a sterilising, cleaning, disinfecting, antiseptic, subcutaneously injectable or preservative end use composition. These diluted compositions are stable for a period of up to 12 months and also require no activation prior to use.

8 Claims, No Drawings

STABLE AQUEOUS GLUTARALDEHYDE SOLUTIONS CONTAINING SODIUM ACETATE AND A NONIONIC DETERGENT

This application is a continuation application of U.S. patent application Ser. No. 08/187,169, filed Jan. 27, 1994, now abandoned, the entire contents of which are hereby incorporated in their entirety.

BACKGROUND OF THE INVENTION

THIS invention relates to a glutaraldehyde composition.

Glutaraldehyde in solution is well known as either a cleaning, disinfecting or sterilizing agent. It has been shown to be a powerful external bacteriocidal, fungicidal and viricidal agent. For glutaraldehyde to be effective as such, however, the pH of the glutaraldehyde solution must be in the range of 7 to 8.5. It is difficult to maintain glutaraldehyde solutions at this pH as they are unstable.

Various stabilisers are currently added to glutaraldehyde solutions just before use by the user to bring the pH into the optimally active range for glutaraldehyde. However, these stabilisers have been found to be skin irritants which, despite the efficacy of glutaraldehyde as a broad spectrum biocide, decreases its desirability as a cleaning and/or sterilizing and/or disinfecting agent. Also, notwithstanding the presence of the stabilizer, glutaraldehyde solutions presently only have a shelf life of two to four weeks at a pH of 7–8.5.

SUMMARY OF THE INVENTION

According to the invention a stable aqueous glutaraldehyde solution comprises:

an aqueous solution of glutaraldehyde (OCH $(CH_2)_3$ CHO);

a non-ionic detergent;

sodium acetate ($NaC_2H_3O_2$); and sufficient of a pH modifier to bring the pH of the solution to 6.0–7.5.

This solution will hereinafter be referred to as "the concentrate".

By "stable" in relation to the concentrate of the invention, it is meant that the concentrate can be stored for a period of up to 6 months without the glutaraldehyde polymerising or the pH dropping below 6.0.

The concentrate preferably comprises 4–6% m/v of glutaraldehyde, more preferably 5% m/v of glutaraldehyde, 19–21% m/v of the non-ionic detergent and as much sodium acetate as is required to buffer the pH of the solution at 6.5 to 7, typically about 0.05 to 0.1% m/v of sodium acetate.

"% m/v" or "mass volume to percentage" as used in this specification means grams of constituent or component in 100 ml of formulation.

Preferably, the concentrate contains sufficient pH modifier to bring its pH to 6.5.

Typically, the sodium acetate used in the concentrate is British Pharmacopeia (B.P.grade) and it is in the form of an aqueous 1% m/v solution which is prepared by dissolving sodium acetate trihydrate in water.

The non-ionic detergent is preferably nonylphenyl ethoxylate, which is typically at a pH of 8.0 to 9.0, and which, together with the sodium acetate, functions as a buffer to maintain the aqueous solution of the invention at the pH of 6 to 7.5.

The pH modifier may be a base, for example it may be a dilate aqueous solution of sodium hydroxide (NaOH). It is preferably a 1N aqueous NaOH solution.

The concentrate of the invention may be diluted to produce an aqueous sterilising, cleaning, disinfecting, antiseptic, subcutaneous injectable or preservative end use composition, having a pH of 6 to 8.5.

By "stable" in relation to the end use compositions of the invention, it is meant that the compositions can be stored for a period of up to 12 months without the glutaraldehyde polymerising or the pH dropping below 6.0 and without requiring any further activation prior to use.

Typically, these compositions are formed by diluting the concentrate of the invention with sterile or potable water at a pH of 7 to 8.5 to provide a composition of reduced glutaraldehyde concentration.

Preferably, the concentration of glutaraldehyde in these diluted, end use compositions is in the region of 2 to 0.05% m/v.

In one embodiment of the invention an aqueous, combined, disinfecting and cleaning composition is provided which comprises sufficient of the concentrate to have a glutaraldehyde concentration of 1% m/v and an amount of sterile or potable water.

The end use compositions may comprise at least one further additive selected from the group consisting of perfumes, dyes, efficacy indicators, deodorisers, propellants, alcohols, soaps, creams and mixtures thereof.

In another embodiment of the invention an aqueous sterilization composition comprises sufficient of the concentrate to have a glutaraldehyde concentration of at least 2% m/v, an amount of sterile or potable water and an efficacy indicator comprising malachite green.

In yet another embodiment of the invention an aqueous subcutaneous injectable composition comprises sufficient of the concentrate to have a glutaraldehyde concentration of from 0.10% to 0.05% m/v and an amount of sterile water.

DESCRIPTION OF PREFERRED EMBODIMENTS

The glutaraldehyde concentrate of the invention is formulated to be stored at a neutral pH of 6 to 7.5 until it is required for an end use application, when it is diluted. Glutaraldehyde is optimally active at a pH of 6 to 7.0 and thus while the concentrate is active, it is unsuitable for end use applications as in this concentrated form it is toxic if ingested. After having been diluted with distilled or potable water, however, it provides biocidally effective compositions which have much reduced toxicity and which have the following end uses: sterilant, antiseptic, sanitisation solutions, cleaning and disinfectant solutions, alcohol swabs, wet wipe cleaning cloths, barrier creams or soaps, aerosol cleaning/disinfectant sprays and subcutaneous injectable solutions.

The concentrate is formed by preparing an initial aqueous solution of glutaraldehyde and adding to it the pH modifier in the form of a sodium hydroxide solution while testing the pH until the pH is in the range of 6 to 8.5. The nonionic detergent, in the form of nonylphenyl ethoxylate is prepared separately by heating it to increase its solubility in the aqueous glutaraldehyde solution and it is then also added to the glutaraldehyde solution. An aqueous solution of sodium acetate, which is prepared separately by dissolving sodium acetate trihydrate in water, is then also added to this solution. The combination of the nonylphenyl ethoxylate and the sodium acetate is important to the invention as it functions as a buffer to stabilise or maintain the pH in this relatively narrow and important range during storage of the concentrate.

The critical feature of the concentrate of the invention is that it is stable for a period of up to 6 months. All previous glutaraldehyde solutions have only been stable from between 2 to 4 weeks because of an alteration in the pH which causes polymerisation of the glutaraldehyde and a resultant decrease in the concentration of aldehyde molecules in solution which in turn causes a decrease in the biocidal activity of the solution.

When diluted as described in more detail below, the end use compositions of the invention will typically have a pH of 6 to 8.5, which is the pH at which glutaraldehyde is optimally activated. At this neutral, or close to neutral pH, the solutions are non-corrosive and non-irritant and hence user friendly as evidenced by the following test results. They also do not damage domestic septic tanks. Also, they do not require the addition of activators prior to use which makes them easy to formulate.

PRIMARY SKIN IRRITATION TESTS OF A COMPOSITION OF EXAMPLE 5 BELOW ON RABBITS

Pine Glutaraldehyde (0.44% m/v)

| | | |
|---|---|---|
| Mean for intact skin at 4 hours for 3 rabbits: | Edema: | 0.333 |
| | Erythema: | 0.000 |
| Mean for abraded skin at 4 hours for 3 rabbits: | Edema: | 0.888 |
| | Erythema: | 0.000 |
| Mean for intact skin at 72 hours for 3 rabbits: | Edema: | 0.000 |
| | Erythema: | 0.000 |
| Mean for abraded skin at 72 hours for 3 rabbits: | Edema: | 0.222 |
| | Erythema: | 0.333 |
| IRRITATION INDEX | = | 1.776 |
| | | 1.776 |
| | | 4 |
| | = | 0.444 |

Lemon Glutaraldehyde (0.2% m/v)

| | | |
|---|---|---|
| Mean for intact skin at 4 hours for 3 rabbits: | Edema: | 0.000 |
| | Erythema: | 0.000 |
| Mean for abraded skin at 4 hours for 3 rabbits: | Edema: | 0.888 |
| | Erythema: | 0.000 |
| Mean for intact skin at 72 hours for 3 rabbits: | Edema: | 0.000 |
| | Erythema: | 0.000 |
| Mean for abraded skin at 72 hours for 3 rabbits: | Edema: | 0.000 |
| | Erythema: | 0.000 |
| IRRITATION INDEX | = | 0.888 |
| | | 0.888 |
| | | 4 |
| | = | 0.222 |

According to the primary irritation index, values of 5 or greater are considered indicative of a positive irritant. In both pine glutaraldehyde and lemon glutaraldehyde the primary irritation index is below 0.5, and therefore the test samples cannot be classified as positive irritants.

A new pair of medical scissors (marked stainless steel) was immersed for approximately two months in a sterilising solution of Example 2. As a control, another pair of the same scissors was immersed in tap water for the same period.

The corrosion tests showed that no corrosion, discolourisation or crevice attack was evidenced after being immersed in the sterilising solution and/or tap water. Therefore, it is clear that the sterilisation solution did not cause corrosion of the instruments.

In various applications, the following minimum and maximum concentrations of glutaraldehyde compositions of the invention are used:

| END USE COMPOSITION | GLUTARALDEHYDE CONCENTRATION |
|---|---|
| Sterilant | minimum of 2% |
| antiseptic | maximum of 0.3% |
| sanitisation solutions | maximum of 2% to 1% |
| cleaning and disinfectant solutions | maximum of 1% |
| alcohol swabs | maximum of 0.2% |
| wet wipe cleaning cloths | maximum of 0.2% |
| barrier creams or soaps | maximum of 0.3% |
| aerosol cleaning/disinfectant sprays | maximum of 0.2% |
| subcutaneous injectable solutions | 0.05 to 0.1%. |

At a 2% concentration, the compositions comprise about 7–9% m/v of the preferred non ionic detergent, nonylphenyl ethoxylate.

A summary of results of stability tests conducted on a sanitising, end use composition of the invention is set out below. As the tests progressed various dyes were added to the solutions to see if this affected the stability of the solutions (glutaraldehyde concentration) and/or the pH. It is clear from the results below that neither were affected.

SUMMARY OF STABILITY TEST RESULTS

| DATE | pH | GLUT CONC | TEST |
|---|---|---|---|
| STORAGE TEMP - 25° C. (ROOM TEMP). | | | |
| NOV 89 | 6.52 | 1.3% | CLEAR |
| FEB 90 | 6.5 | 1.29% | CLEAR |
| MAY 90 | 6.53 | 1.25% | CLEAR |
| AUG 90 | 6.49 | 1.27% | CLEAR |
| NOV 90 | 6.5 | 1.25% | CLEAR |
| FEB 90 | 6.51 | 1.24% | CLEAR |
| STORAGE TEMP - 32° C. | | | |
| NOV 89 | 6.5 | 1.31% | CLEAR |
| FEB 90 | 6.5 | 1.26% | CLEAR |
| MAY 90 | 6.5 | 1.20% | CLEAR |
| AUG 90 | 6.47 | 1.22% | SLIGHT YELLOW (added dye) |
| NOV 90 | 6.52 | 1.23% | SLIGHT YELLOW (added dye) |
| FEB 90 | 6.5 | 1.20% | SLIGHT YELLOW (added dye) |
| STORAGE TEMP - 25° C. (ROOM TEMP). | | | |
| MAY 91 | 6.53 | 1.25% | GREEN (added dye) |
| MAY 91 | 6.52 | 1.23% | YELLOW (added dye) |
| AUG 91 | 6.45 | 1.27% | GREEN (added dye) |
| AUG 91 | 6.49 | 1.25% | YELLOW (added dye) |
| STORAGE TEMP - 32° C. | | | |
| MAY 91 | 6.5 | 1.26% | GREEN (added dye) |
| MAY 91 | 6.49 | 1.25% | YELLOW (added dye) |
| AUG 91 | 6.47 | 1.23% | GREEN (added dye) |
| AUG 91 | 6.49 | 1.23% | YELLOW (added dye) |

As mentioned above, the end use compositions of the invention are not highly toxic. Various toxicity tests, as set out below, at different concentrations for the compositions of Examples 2 and 5, hereafter, were conducted.

Human patch tests on skin, intermittent skin contact tests, inhalation tests and eye contact tests were conducted. It was found that although eye contact must be avoided, the product is safe at 2%, 1% and less in concentration.

In oral toxicity tests the following results were achieved.
LD50 1.87 ml/kg at 25%—Potentially toxic
LD50 2.00 ml/kg at 5%—mildly toxic
Swallowing or inhalation of a 2% glutaraldehyde composition of Example 2 or 5 was found to irritate mucous membranes of test animals. However, all animals experimented on survived the test. An autopsy was done after the testing lethal dose concentrations of greater than 2% on animals. The animals showed lung tissue damage. It is clear, therefore, that concentrations of greater than 2% are potentially toxic for internal use.

An acute toxicity study on glutaraldehyde ammonia reaction products showed them to be non toxic and totally biodegradable.

The following are illustrative examples of the various end use compositions of the invention.

EXAMPLE 1

CONCENTRATE

A 5% m/v glutaraldehyde aqueous concentrate was formulated as follows:

| Ingredients | % m/v |
|---|---|
| glutaraldehyde 25% | 5 |
| nonylphenyl ethoxylate | 20 |
| 1N aq. NaOH solution (pH modifier) | sufficient for pH adjustment to 6.0–7.0 (optimal 6.5) |
| 1% m/v aqueous sodium acetate solution | 0.1–0.05 |
| water | sufficient to make up 100 ml |

The 1% m/v aqueous sodium acetate solution was prepared by dissolving sodium acetate trihydrate B.P. grade in water to form a 1% m/v stock solution of it and this was further diluted to give the formula requirements above.

The glutaraldehyde used was that available in South Africa as either a 25% or 50% aqueous solution under the name "UCARCIDE" from Union Carbide South Africa Ltd.

The 5% m/v aqueous concentrate was prepared by mixing the "UCARCIDE" with water to form a solution followed by adjustment of the pH of the resulting solution with the NaOH solution. The nonylphenyl ethoxylate was heated to 50° C. and then added with thorough mixing. Once the solution was at room temperature the 1% m/v aqueous sodium acetate was added with mixing. Optionally perfume (0.1 m/v) and a food colouring dye (0.1 m/v) could then be added with mixing.

The 5% m/v concentrate of glutaraldehyde can be stored for a period of 6 months at room temperature (25° C.).

An H.I.V (virus) TEST was performed by the Virology Department of Stellenbosch University. These tests were conducted in the laboratory using viable virus imported from the Louis Pasteur Institute Paris. Tests were conducted in blood/organic matter containing up to 20% serum. Tests showed that the concentrate of Example 1, diluted to 0.05%, inactivated the virus in the presence of organic matter within 5 mins, external to the body. Tests were carried out on fresh and 12 month old products.

The 5% m/v concentrate could be diluted appropriately with sterile or potable water to provide, for example, 1% m/v, 2% m/v, 0.3% m/v, 0.2% m/v, 0.1% m/v and 0.05% m/v end use compositions in which the glutaraldehyde is activated to its optimal effective pH range of 7.0–8.5.

The 2% or less end use compositions can be stored at a pH of 6.0–8.5 (6.5 optimal) for a period of 12 months.

EXAMPLE 2

STERILANT AND SANITISATION COMPOSITION FOR MEDICAL PURPOSES

A sterilant or sanitisation solution was formulated by dilution of the 5% m/v concentrate prepared as described in Example 1 to 2% m/v glutaraldehyde and then adding 0.01% m/v of an antiseptic efficacy dye known as B.P. grade malachite green. This dye is activated by the presence of aldehyde groups to a blue colour. Thus, when the sterilising solution loses its colour, this is an indication that the glutaraldehyde solution is no longer active.

This solution was suitable for storage for up to 12 months and could be used as such without dilution, or by further dilution with sterile or potable water, for medical applications, for example for a surgery, operating theatre, intensive care ward or for general use. It will be appreciated that a bulk 2% composition can be further diluted to differing concentrations to provide various end use compositions, for sterilising instruments (2% concentrate) for disinfecting body fluid spillage or heavily contaminated areas (0.5%), for general light duty cleaning of any surface (eg wards) (0.2%).

EXAMPLE 3

AN ANTISEPTIC COMPOSITION

The 2% composition of Example 2 is suitable as an antiseptic solution when diluted with deionised water to a concentration of 0.3% m/v.

EXAMPLE 4

SUBCUTANEOUSLY INJECTABLE DISINFECTANT COMPOSITION

The 2% composition of Example 2, without the dye, is suitable as a subcutaneous injectable composition when diluted to a concentration of 0.10% m/v to 0.05% m/v with sterile water and prepared without using any heat. The composition is sterilized by filtration. The purpose of this injectable composition is as a precaution against infection after skin trauma, typically by medical professionals who are injured while dealing with infected patients. The composition is locally injected around the skin lesion and provides some protection against infection of cuts and wounds by contaminated needles and other medical instruments.

EXAMPLE 5

CLEANING/DISINFECTANT COMPOSITION FOR INDUSTRIAL OR CONSUMER APPLICATIONS

A cleaning disinfectant concentrate suitable for industrial or consumer applications was formulated as follows:

| INGREDIENTS | % M/V |
|---|---|
| glutaraldehyde | 1 |
| nonylphenyl ethoxylate | 8 |
| perfume | 0.01 |
| food colouring dye | 0.01 |
| 1N aq. NaOH solution | sufficient to adjust pH to 6.0–6.5 |
| 1% sodium acetate trihydrate solution | 0.1 to 0.5 |
| water | sufficient to make up 100 |

As in Example 2, this composition is suitable for storage for up to 12 months and can also be further diluted with sterile or potable water. In the household environment a further 10 times dilution for end uses, for example washing dishes is optimal.

Trials using this composition were completed successfully in the following environments: Pathology laboratory cleanliness; Microbiology Total Counts of Dairy Farmers equipment sanitisation; Veterinary animal pens cleanliness; Comparative study of formalin versus "KLEENOX" (registered trade mark) versus Glutaraldehyde against I.B.D.

virus. (Poultry Gambro disease); Chicken hatchery cleanliness trials; Pharmaceutical equipment and filling room cleanliness; Chocolate manufacturing filling machines sanitisation; Cleaning of ladies' and gents' rooms and offices; School facilities; Hotel dishwashers and washing machines; Cleaning of printer's rollers of printing machines; Doctors; rooms and cleaning of a medical centre; Industrial, canteen and employee quarters cleaning; and Cleaning of garage mechanics' hands.

EXAMPLE 6A

An alcohol swab was made using a composition formulated by diluting the 5% m/v concentrate of Example 1, 25 times with a 10% to 12% v/v solution of isopropyl alcohol in water to form a 0.2% m/v glutaraldehyde solution.

EXAMPLE 6B

An alcohol swab similar to that of Example 6A was made by substituting ethyl alcohol for the isopropyl alcohol. Optionally, a perfume can be added to the solution.

EXAMPLE 7

A cleaning solution suitable for making a disinfectant wet-wipe cleaning cloth was formulated by diluting the 5% m/v concentrate of Example 1, 25 times with water to give a 0.2 m/v% glutaraldehyde solution. A perfume (0.01% m/v) was optionally added. The wet wipe cloth was pre-impregnated with a metabisulphate solution by soaking in a 0.1% sodium metabisulphate solution, which acts as a reducing agent to prevent, or at least inhibit, oxidation and hence discolouration of the wet wipe during storage or in use, and then allowed to dry. The wet wipes were subsequently impregnated with a 0.05% to 2.0% m/v glutaraldehyde solution by placing in containers containing the glutaraldehyde solution.

EXAMPLE 8A

An aerosol spray for antiseptic/disinfection uses was formulated by diluting the 5% m/v concentrate of Example 1, 25 times with a 65% v/v solution of dimethyl ether (propellant) in water to form a 0.2% m/v glutaraldehyde spray. An anti-tobacco deodoriser (0.1%) sold as formulation 77317C by Haarmann and Reimer was added to the formulation and optionally a perfume (0.01% m/v) was added.

EXAMPLE 8B

An aerosol spray for pathology laboratories for disinfecting laboratory bench tops after blood spills was formulated as above. It does not contain perfume or anti-tobacco deodoriser.

EXAMPLE 9

A standard, non-aqueous barrier cream B.P. and a standard liquid soap were made up including the concentrate of Example 1. The barrier cream/soap had a concentration of 0.3% m/v of glutaraldehyde. They had the following respective formulations:
HAND SOAP 1. Sodium Lauryl Sulphate
2. Pearling agent (mixture of anionic and nonionic components and glycerol monostearate).
3. Sodium chloride
4. Alkyldimethyl amine oxide 5. Polyol fatty acid ester
6. 0.3% glutaraldehyde
7. Perfume (floral)
8. Dye (pink).

BARRIER CREAM

1. Potassium hydroxide
2. Sorbitol
3. Dimethyl polysiloxane oil
4. Stearic acid
5. Lemon perfume
6. 0.3% Glutaraldehyde.

It is an advantage of the invention as described in the above Examples that the solutions provide an effective cleaner and disinfectant in one solution. Since the solutions have a substantially stable neutral pH, they are non-corrosive and user-friendly for employee and householder use. Also, the 2% or less compositions are stable for a period of 12 months at storage room temperatures (25° C.). In addition, a solution having a concentration of glutaraldehyde of less than 2% is not a skin irritant nor does it require an activator prior to use. Their biocidal effects are very important, as evidenced by the tests set out below. Also the 2% concentrate is sporicidal and is therefore useful for sterilising medical instruments.

The following E.P.A. (Environmental Protection Agency) equivalent sanitisation tests were also carried out using the compositions of Examples 2 and 5.

Stainless steel, aluminium, brass, chrome, glass, glazed and unglazed ceramic tiles, linoleum floor tiles, latex rubber, polyethylene, painted and unpainted wood were exposed to a concentration of $2.3 \times 10^6$ organisms of *Staphylococcus aureus* (ATCC 6538) and *Klebsiella pneumoniae* (ATCC 4352). They were then wiped with a cleaning cloth containing a cleaning solution of Examples 2 and 5.

Total organism kill was observed.

The composition of Example 2 had proven efficacy against the following microorganisms. (References to the test methods or the organizations/institutions which conducted the tests are given at the end of the list.)

| | |
|---|---|
| *Escherichia Coli* (3)(1) | Rotavirus SA-11 (6) |
| *Salmonella Typhi* (6) | *Legionalla Pneumophilia* (4) |
| *Staphylococcus Aureus* (3)(1) | Mycobacterium SPP (4) |
| *Salmonella Pollorum* (6) | *Bacillus Anthracis* (6) |
| New Castle disease virus (2)(6) | *Clostridium Tetani* (6) |
| Influenza (2)(6) | *Clostridium Bifermentans* (6) |
| Coxsackie virus (2) (6) | *Clostridium Sporogenes* (6) |
| Hepatitis B virus (6) (4) | *Bascillus Phmilis* (6) |
| *Bacillus Subtilis* (5) (4) | *Proteus Vulgaris* (6) |
| Equine Infectious anemia virus (6) | Poliomyelitis virus type 1 Mahoney strain (6) |
| *Pseudomonas Aeruginosa* (3) (5) (1) | *Desulfovibrio desulfuricans* (6) |
| *Proteus Rettgeri* (6) | Desulforomaculum SP (6) |
| *Trichophyton Gypseum* (6) | *Mucor Hiemalis* (6) |
| *Microsporum Gypseum* (6) | *Rhizopus Stolonifer* (6) |
| *Candida Albicans* (11) | *Aspergillus Niger* (5) (6) |
| *Enterobacter Cloaca* (6) | *Penicillium Chrysogenum* (6) |
| Infectious Bursal disease virus (7) (6) | *Saccharomyces Cereviseae* (6) |
| Avian Reovirus (6) | *Trichophyton Mentagrophytes* var interdigitale (6) |
| *Klebsiella pneumonial* (8)(4) | *Sporothrix Schenchlaii* (10) |
| HIV virus 1 (Aids) (9) | |

TEST METHODOLOGIES

| | |
|---|---|
| (1) SABS 261 | (2) AOAC (American Standard Analytical Chemical Test Methods) |
| (3) American Type Culture Collection | (4) Union Carbide/EPA equivalent test |

| | |
|---|---|
| ATCC 6538 SABS 639 modified | |
| (5) Kelsey Sykes Test SABS | (6) Union Carbide (USA) |
| (7) Onderstepoort (SA) | (8) ATCC 4352 Microorganism standard |
| (9) Stellenbosch University (SA) | (10) SABS 433-195 SATCC 352 (South African Type Culture Collection) |
| (11) SABS 433–1953 SATCC 354 | (12) Medical Research Council of SA |
| (13) Pretoria University Dept of Poultry Diseases | |

More particularly, the test for *Mycobacterium tuberculosis* was conducted under the following conditions.

| | |
|---|---|
| a) Dilutions of sample: | 2%, 0.5% and 0.2% |
| b) Diluent: | Sterile water |
| c) Temperature of test: | 22° C. |
| d) Test Organism: | *Mycobacterium tuberculosis* |
| e) Test organism load: | Approximately $10^7$ organisms per 1.0 ml |
| f) Exposure time: | 10, 20 and 30 min |
| g) Inactivator: | A suitable fluid inactivator |
| h) Counting medium: | Lowenstein Jensen medium |

METHOD OF TEST

The sample was tested in accordance with the Proposed Standard Specification for Disinfectants based on Glutaraldehyde for use in Medical Instruments.

RESULTS

| Sample | Exposure time (min) | Dilutions | Percentage kill of *M. tuberculosis* |
|---|---|---|---|
| G-Cide Sterilising Solution | 10 | 2% | 99.99 |
| | 20 | | 99.99 |
| | 30 | | 99.99 |
| | 10 | 0.5% | 99.99 |
| | 20 | | 99.99 |
| | 30 | | 99.99 |
| | 10 | 0.2% | 99.7 |
| | 20 | | 99.99 |
| | 30 | | 99.99 |

Note

When tested in accordance with Subsection 6.2, the prescribed concentration of the disinfectant shall kill at least 99.99% of the organisms within the given time limits.

*P. aeruginosa*—5 min

*a. niger*—15 min

Spores of *B. subtilis* var globigii—4 h

More particularly, the Kelsey Sykes test (5) and an efficacy test, using *Pseudomonas aeruginosa*, *Aspergillus niger* and *Bacillus subtilis* spores as test organisms was conducted under the following conditions.

METHOD OF TEST

Four composition samples A,B, C and D were tested in accordance with the Proposed Standard Specification for Disinfectants based on Glutaraldehyde.

Results

KELSEY SYKES TEST (MODIFIED)

| Organism | Condition of test | Contact time | A | B | C | D |
|---|---|---|---|---|---|---|
| *B. subtilis* spores | Clean | 4 h | — | — | — | — |
| | Clean | 8 h | — | — | — | — |
| *P. aeruginosa* | Clean | 8 min | — | — | — | — |
| | | 18 min | — | — | — | — |
| | Dirty | 8 min | — | — | — | — |
| | | 18 min | — | — | — | — |

EFFICACY TEST

Number of viable surviving units of

| Contact time | *P. aeruginosa* | | | | *A. niger* | | | | *B. subtilis* spores | | | |
|---|---|---|---|---|---|---|---|---|---|---|---|---|
| | A | B | C | D | A | B | C | D | A | B | C | D |
| 5 min | 0 | 0 | 0 | 0 | | | | | | | | |
| 15 min | | | | | 0 | 0 | 0 | 0 | | | | |
| 4 h | | | | | | | | | 0 | 0 | 0 | 0 |
| Control | $1.8 \times 10^6$ | | | | $1.7 \times 10^6$ | | | | $3.4 \times 10^6$ | | | |

| A | B | C | D |
|---|---|---|---|
| pH VALUE | | | |
| 6.1 | 6.7 | 5.6 | 5.7 |
| ALUMIMUM CORROSIVENESS | | | |
| PASS | PASS | PASS | PASS |
| RINSING PROPERTIES | | | |
| PASS | PASS | PASS | PASS |
| WATER-INSOLUBLE MATTER CONTENT | | | |
| 0.03 | 0.03 | 0.03 | 0.02 |

I claim:

1. An aqueous glutaraldehyde concentrate solution consisting essentially of:

a 4–6% m/v aqueous solution of glutaraldehyde;

a 19–21% m/v nonyl phenyl ethoxylate non-ionic detergent;

a sufficient amount of a pH modifier to bring the solution to a pH range of 6–7.5; and sodium acetate trihydrate in an amount that, with said nonyl phenyl ethoxylate, serves to buffer the solution at said pH range;

wherein the solution can be stored for a period of up to six months without the glutaraldehyde polymerising or the pH dropping below 6.

2. A solution according to claim 1, wherein said aqueous glutaraldehyde solution has a concentration of 5% m/v and said sodium acetate trihydrate has a concentration of 0.05 to 0.1% m/v.

3. A solution according to claim 1 wherein the pH modifier is a base.

4. A solution according to claim 3 wherein the base is a 1N aqueous NaOH solution.

5. A solution according to claim 4 which contains sufficient NaOH to bring its pH to 6.5.

6. An aqueous glutaraldehyde end use solution consisting essentially of:

a 0.05–2% m/v aqueous solution of glutaraldehyde;

a 7–9% m/v nonyl phenyl ethoxylate nonionic surfactant a sufficient amount of a pH modifier to bring the solution to a pH range of 6 to 8.5; and sodium acetate trihydrate in an amount that, with said nonyl phenyl ethoxylate, serves to buffer the solution at said pH range;

wherein the solution can be stored for a period of up to twelve months without the glutaraldehyde polymerising or the pH dropping below 6.

7. An aqueous, disinfecting and cleaning composition according to claim 6, wherein said aqueous glutaraldehyde solution has a concentration of 1% m/v.

8. A disinfecting and cleaning wipe comprising a substrate pre-impregnated with an effective amount of sodium metabisulphate to reduce discolouration of the wipe and subsequently impregnated with a sufficient amount of the composition according to claim 7 to have a glutaraldehyde concentration of at maximum 2% m/v.

* * * * *